United States Patent [19]

Tatebayashi et al.

[11] Patent Number: 5,150,704
[45] Date of Patent: Sep. 29, 1992

[54] LASER THERAPEUTIC APPARATUS

[75] Inventors: Tsuneo Tatebayashi; Yoshio Uno; Masaichi Hiei, all of Kanagawa, Japan

[73] Assignee: Fuji Electric Co., Ltd., Kanagawa, Japan

[21] Appl. No.: 355,103

[22] Filed: May 18, 1989

Related U.S. Application Data

[63] Continuation of Ser. No. 64,651, Jun. 22, 1987, abandoned.

[30] Foreign Application Priority Data

| | | | |
|---|---|---|---|
| Jun. 23, 1986 | [JP] | Japan | 61-146680 |
| Jul. 15, 1986 | [JP] | Japan | 61-165890 |
| Jul. 15, 1986 | [JP] | Japan | 61-165891 |
| Jul. 15, 1986 | [JP] | Japan | 61-165892 |
| Jul. 15, 1986 | [JP] | Japan | 61-165893 |
| Jul. 15, 1986 | [JP] | Japan | 61-165894 |
| Jul. 24, 1986 | [JP] | Japan | 61-174091 |
| Jan. 9, 1987 | [JP] | Japan | 62-2702 |

[51] Int. Cl.⁵ .................................................. A61N 5/06
[52] U.S. Cl. ........................................ 128/395; 606/2; 606/10; 606/11; 606/13; 606/17; 606/19
[58] Field of Search ............... 128/303.1, 395-398; 606/2, 9-19

[56] References Cited

U.S. PATENT DOCUMENTS

| | | | |
|---|---|---|---|
| 1,429,443 | 9/1922 | McFaddin | 128/395 |
| 1,637,421 | 8/1927 | Lipschutz | 128/744 |
| 1,739,509 | 1/1929 | Goodrich | 128/395 |
| 2,560,652 | 7/1951 | Landauer | 128/396 |
| 3,622,743 | 11/1971 | Muncheryan | 128/303.1 |
| 4,215,694 | 8/1980 | Isakov et al. | 128/303.1 |
| 4,313,431 | 2/1982 | Frank | 128/303.1 |
| 4,388,924 | 6/1983 | Weissman et al. | 128/303.1 |
| 4,473,074 | 9/1984 | Vassiliadis | 128/303.1 |
| 4,619,249 | 10/1986 | Landry | 128/397 |
| 4,633,870 | 1/1987 | Sauer | |
| 4,718,416 | 1/1988 | Nanaumi | 128/303.1 |

FOREIGN PATENT DOCUMENTS

| | | | |
|---|---|---|---|
| 968854 | 6/1975 | Canada | 128/395 |
| 130950 | 1/1985 | European Pat. Off. | 128/303.1 |
| 184530 | 6/1986 | European Pat. Off. | 128/395 |
| 190107 | 8/1986 | European Pat. Off. | 128/303.1 |
| 2820908 | 11/1978 | Fed. Rep. of Germany | 128/303.1 |
| 2827639 | 1/1979 | Fed. Rep. of Germany | 128/303.1 |
| 2740969 | 3/1979 | Fed. Rep. of Germany | 128/398 |
| 2937598 | 3/1981 | Fed. Rep. of Germany | 128/395 |
| 3218739 | 12/1982 | Fed. Rep. of Germany | 128/303.1 |
| 2513522 | 4/1983 | France | 128/395 |
| 2571264 | 4/1986 | France | 128/395 |
| 651477 | 9/1985 | Switzerland | 128/395 |
| 2184021 | 6/1987 | United Kingdom | 128/303.1 |

OTHER PUBLICATIONS

"Fiber Bundle Scanner for Laser Photocoagulation Treatment" by Fujii et al, Optics & Laser Tech. Feb. 1982, pp. 39-40.

Primary Examiner—David M. Shay
Attorney, Agent, or Firm—Finnegan, Henderson, Farabow, Garrett and Dunner

[57] ABSTRACT

A laser therapeutic apparatus for treating a patient by irradiating selected body parts by laser beams generated by a plurality of laser probes. The laser probes are supported by a common support table and a lock mechanism is provided to selectively lock and release the laser probes to maintain and release the orientation thereof. Each laser probe includes an inner cylinder and an outer cylinder and a spring for biasing the inner cylinder axially within the outer cylinder. The end of the inner cylinder is provided with one or more lights that are energized when the associated probe is emitting a laser beam. The end of each laser probe further includes indicating rings for visually indicating the extent of the axial movement of the inner cylinder with respect to the outer cylinder.

21 Claims, 15 Drawing Sheets

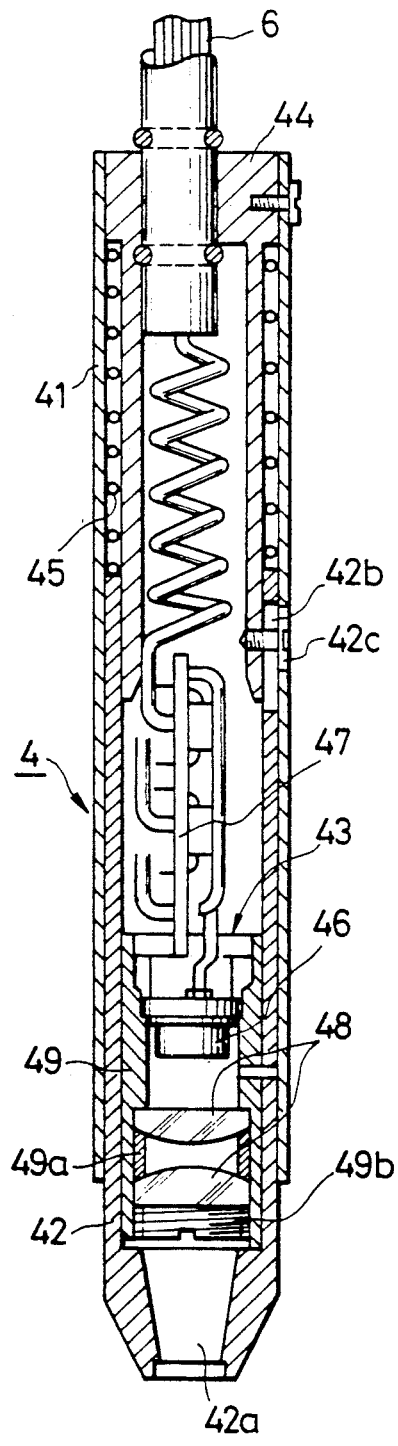
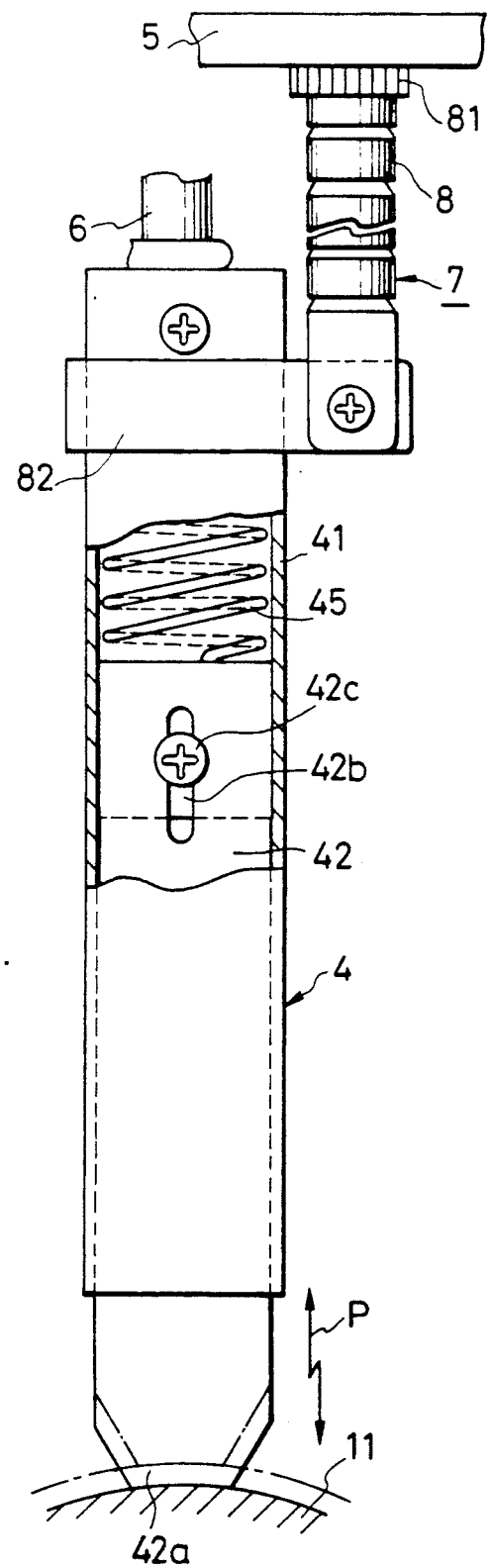
FIG. 11
FIG. 12

FIG. 21

| STAGE NO 3. NS | IRRADIATION TIME TS | IRRADIATION IN DENSITY PER PROBE (P1-P20) | | | | | |
|---|---|---|---|---|---|---|---|
| | | P1 | P2 | P3 | P4 | ~ INTENSITY | P20 |
| 1 | 3 | 10 | 10 | 0 | 0 | | 0 |
| 2 | 3 | 0 | 0 | 8 | 8 | | 0 |
| 3 | 2 | 0 | 8 | 8 | 0 | | 0 |
| 4 | 0 | | | | | | |
| ~ | ~ | ~ | ~ | ~ | ~ | ~ | |
| 10 | | | | | | | |

LASER THERAPEUTIC APPARATUS

This application is a continuation of application Ser. No. 07/064,651, filed Jun. 22, 1987, now abandoned.

FIELD OF THE INVENTION

The present invention relates to a laser therapeutic apparatus for relieving pain and inflammation by using laser beams irradiated from probes arranged on or near the affected areas of the body.

BACKGROUND OF THE INVENTION

A laser therapeutic apparatus has been developed and put to practical use for treating persons suffering from stiff shoulders, neuralgia, arthritis, and the like, by irradiating each affected body part or treatment spot with a laser beam. A conventional laser therapeutic apparatus of this sort usually comprises a probe from which a laser beam is irradiated and a control box including a power supply switch, an output knob for regulating the intensity of the laser beam, and a timer for setting irradiation time. The irradiation probe is connected to the control box by a cord. Accordingly, after the laser beam is set in a suitable irradiation mode by the control box, the affected body part is irradiated by the irradiation probe to treat the ailment.

The conventional laser therapeutic apparatus is equipped with one irradiation probe. From a clinical standpoint, however, there are very often many affected parts or affected spots for applying treatment. Since the conventional laser therapeutic apparatus is designed to irradiate only one location at a time, it frequently takes a very long time to treat a patient. This lowers the efficiency of the treatment, and is further disadvantageous in that the treatment time required of the doctors is increased. Not only has such treatment been costly, it has caused patients to suffer pain and discomfort unnecessarily during the lengthy medical treatment.

OBJECTS AND SUMMARY OF THE INVENTION

An object of the present invention is to increase the efficiency of laser therapy.

Another object of the present invention is a laser therapeutic apparatus for treating several affected areas of a patient simultaneously to improve the efficiency of the treatment, to reduce, the amount of time of doctors in such treatments, and to reduce the pain and discomfort of a patient by reducing the length of treatment.

These and other objects are attained by laser therapeutic apparatus comprising a power supply switch for supplying power, a plurality of laser probes selectively energized with the power, a plurality Of cords for connecting the laser probes to the power supply switch, and a control section including means for selecting the irradiation time and the irradiation output of each of the laser probes and for controlling the energization of the laser probes in accordance with the selected irradiation times and irradiation outputs.

BRIEF DESCRIPTION OF THE DRAWINGS

The manner by which the above objects, and other objects, features, and advantages of the present invention are attained will be apparent from the following detailed description and the drawings wherein:

FIG. 11 is a sectional block diagram of the probe of FIG. 7;

FIG. 12 is a diagrammatic illustration of a probe during operation;

FIG. 21 is an illustration of a therapeutic pattern set up through the operating, panel of FIG. 19.

DETAILED DESCRIPTION OF THE PREFERRED EMBODIMENT

Figure 1:
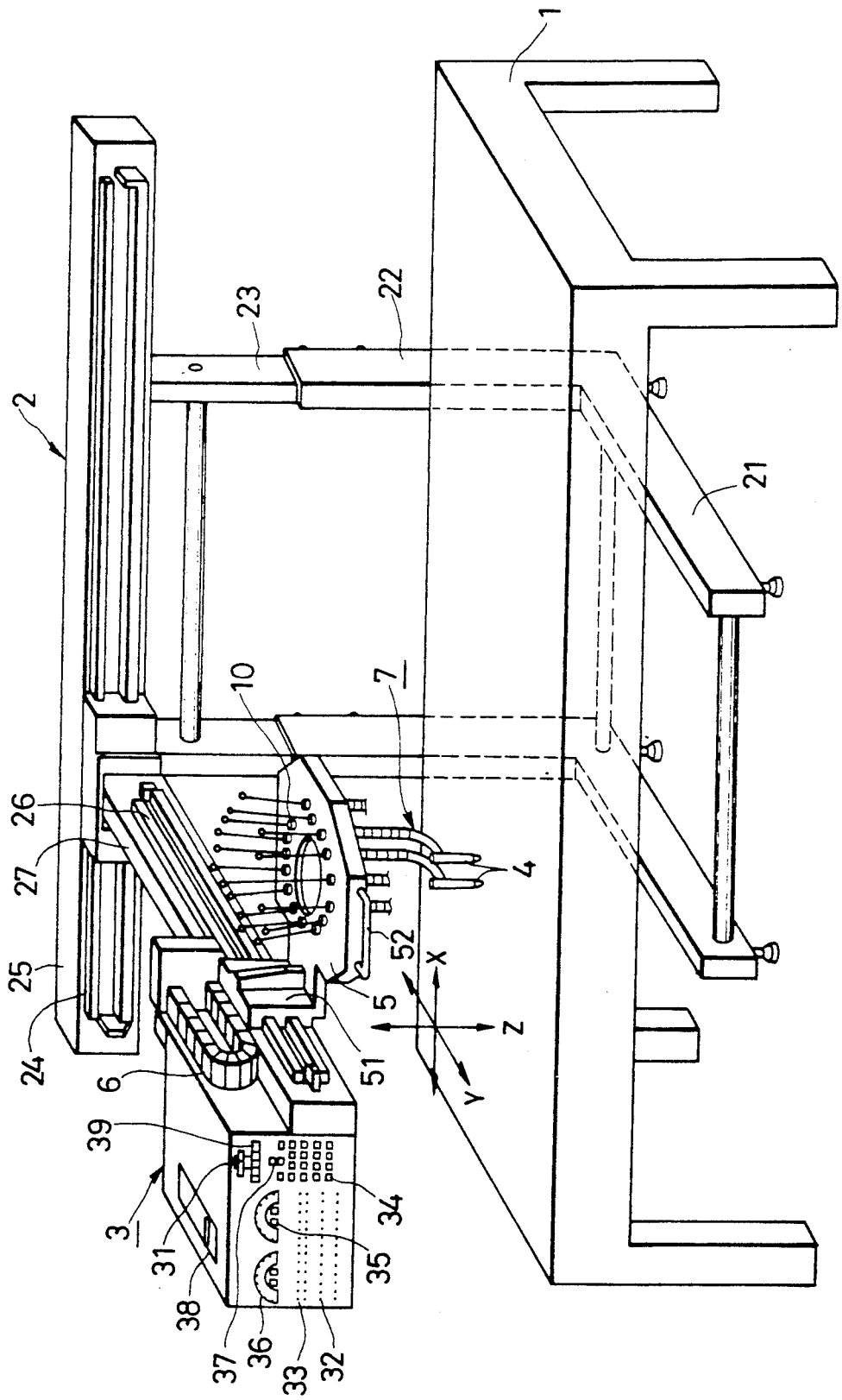
FIG. 1 is a perspective view of a laser therapeutic apparatus embodying the present invention.
Figure 2:
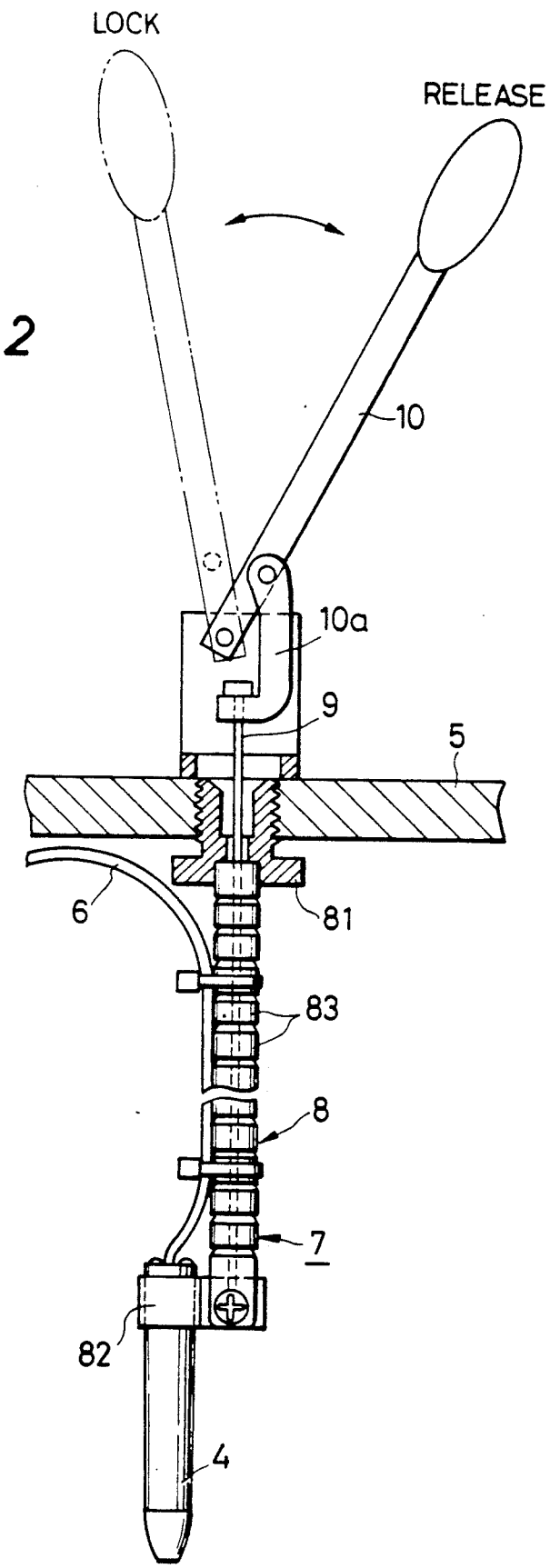
FIG. 2 is a sectional block diagram of a probe support mechanism.
Figure 3:
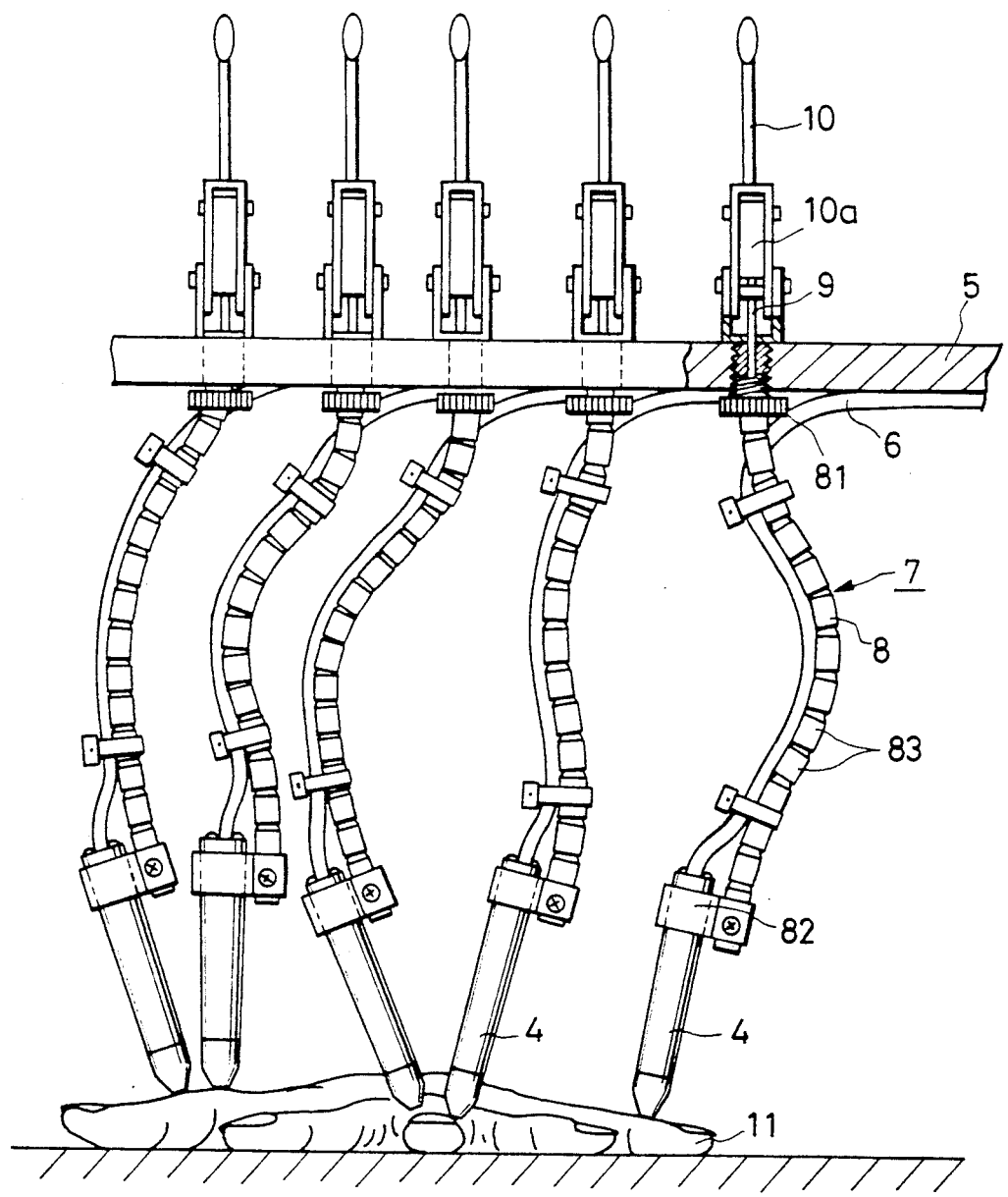
FIG. 3 is a diagram of multichannel probes applied to affected body parts in a therapeutic state.

Referring now to FIGS. 1 through 3, the overall construction of the laser therapeutic apparatus will be described. FIG. 1 shows a bed 1 for a patient and a laser therapeutic apparatus according to the preferred embodiment including a trestle 2 installed above and to one side of the bed 1, a control board 3, multichannel probes 4, and a probe support table 5. The trestle 2 comprises base members 21, vertical rails 22 extending from the base members 21, and support frames 23 fitted into and supported with the vertical rails 22 as guides.

A frame 25 is equipped with horizontal rails 24 and is fixed to the support frames 23. A second frame 27 extends transversely from the frame 25 and is supported by a truck that is supported by the horizontal rails 24. Horizontal rails 26 are mounted on the frame 27.

The frame 27 is fitted with the control board 3 and the probe support table 5 is movably supported by the longitudinal rails 26 through a support head 51 and further the multichannel probes 4 are individually supported through probe support mechanisms as later described in detail. The probe support table 5 can be moved along the X-, Y-, and Z- axes (shown by arrows of FIG. 1) by means of the rails 24 and 26 and the vertical support member 22, respectively. A handgrip 52 is fitted on the front edge of the probe support table 5 and may be used in moving the probe support table 5.

The control board 3 incorporates a power supply and a variety of control devices and operating equipment for setting a laser beam irradiation mode. The front panel of the board 3 has a power supply switch 31, selective irradiation switches 32 corresponding to the multichannel probes 4, irradiation display lamps 33, various function keys 34 for setting the irradiation mode, a scale plate or dial 35 for use in setting irradiation time, a scale plate or dial 36 for use in grouping the probes, an irradiation start switch 37, and a printer 38 for printing out therapeutic data, patient numbers, therapeutic dates, irradiation time, etc.

The control board 3 is connected to the probe 4 of each channel through a wiring cord 6. In this case, a multicore cable built of integrated multichannel wiring cords 6 is employed to connect the control board 3 to each of the probes 4.

Parallel flexible pipes 8 (FIG. 2) are provided on the undersurface peripheral area of the probe support table 5 as flexible support arms respectively corresponding to the multichannel probes 4. In this case, the fitting bases of the parallel flexible pipes 8 are suspended from the undersurface of the table 5 through adjusting screws 81. The probes 4 are supported by the front ends of the flexible pipes 8 through holders 82 on channel bases. Each flexible pipe 8 operates as a flexible support arm and is built from a number of serially-connected pipe segments 83 continuously coupled together in the form of a flexible joint and flexible in every direction in an unrestricted state.

A wire 9 passes through each of the flexible pipes 8. The front end of each wire 9 is fixed to the front end of the flexible pipe 8 and each wire 9 passes through the probe support table 5 and is coupled at its other end to a clamp lever 10 fitted to the surface of the probe support table 5 through a coupling link 10a. Each clamp lever 10 is used to apply and release tension in the corresponding wire 9. When the clamp lever 10 is placed in a release position (shown by a continuous line in FIG. 2) it releases tension from the wire to free the movement of the flexible pipe 8. When the clamp lever 10 is rotated to a lock position (shown by the alternate long and two short dashes line) the wire 9 is stretched to apply pressure to each segment 83 of the flexible pipe 8 and to restrict movement thereof. As a consequence, if the clamp lever 10 is moved from the release position to the lock position after the flexible pipe 8 is bent into a given orientation or shape while it is in the free state, the flexible pipe 8 will maintain that shape. The amount of tension that can be applied to the wire 9 resulting from the operation of the clamp lever 10 may be adjusted by turning the adjusting screw 81 of the flexible pipe 8 to change the relative position of the flexible pipe 8 with respect to the clamp lever 10. This adjusting operation may initially be conducted once. The cord 6 of the probe is supported along the flexible pipe 8 by means of clamp pressure.

The operation of the laser therapeutic apparatus during the actual provision of treatment will subsequently be described. In the standby state, the clamp lever 10 of the probe support mechanism is set in the release position and each of the multichannel probes 4 is freely suspended from the undersurface of the probe support table 5 in the unrestricted state through the corresponding flexible pipes 8. With the patient reclining on the bed 1, the doctor or operator manipulates the handgrip 52 of the probe support table 5 to move the probe support table 5 close to the affected body part or the effective spot for applying the treatment, e.g., the knee, wrist, or ankle joint regions. Subsequently, as shown in FIG. 3, the operator bends the flexible pipes 8 as necessary on a channel basis to position the laser beam irradiation end of each probe 4 until it contacts or is in the proper position with respect to the part of the body that needs treatment. In that state, the operator rotates each clamp lever 10 to the lock position to lock the flexible pipes 8 in their bent posture. The probes 4 of the selected channels are thus properly positioned with respect to the parts of the body to be treated to complete the probe setting.

The operator then individually sets the optimum irradiation mode for each of the probes 4 including the laser irradiation output, irradiation time, etc., which are dependent on the type of body part to be treated and the condition of the affected body part. The irradiation mode data is set by means of the control board 3. The operator then turns on the selective switch 32 and the irradiation start switch 37, to start the irradiation of laser beams from the probes 4 to the affected body part. Whether the laser beams are irradiated from the probes of the selected channels simultaneously and collectively or successively in a given order can be selected according to programming through the control board 3. Moreover, the irradiation display lamps 33 are caused to blink during laser beam irradiation and, when the laser beam irradiation is terminated after a designated period of time has lapsed, the lamps 33 will remain off. The doctor or operator resets the control board 3 and obtains various printed therapeutic data from the printer 38. The flexible pipes 8 supporting the probes 4 may be restored to the unrestricted, i.e., freely movable, positions by rotating each clamp lever 10 of the probe support mechanism to the release position.

Since the probes are all supported from the table through the corresponding flexible pipes, the multichannel probes can be readily set to the positions for effectively treating the affected body parts in part by positioning the moving probe support table 5. Each flexible support arm 8 has a front end for supporting the probe of each channel, a back end fixed to the undersurface of the probe support table 5, and an associated clamp mechanism for locking the support arm 8 in a given orientation or state. Moreover, there is no need for further manipulation after the probes have once been set. The set positions can be held during the period of treatment, and since multiple probes may be used simultaneously, the doctor or operator is allowed to provide efficient labor-saving treatment.

Figure 4:
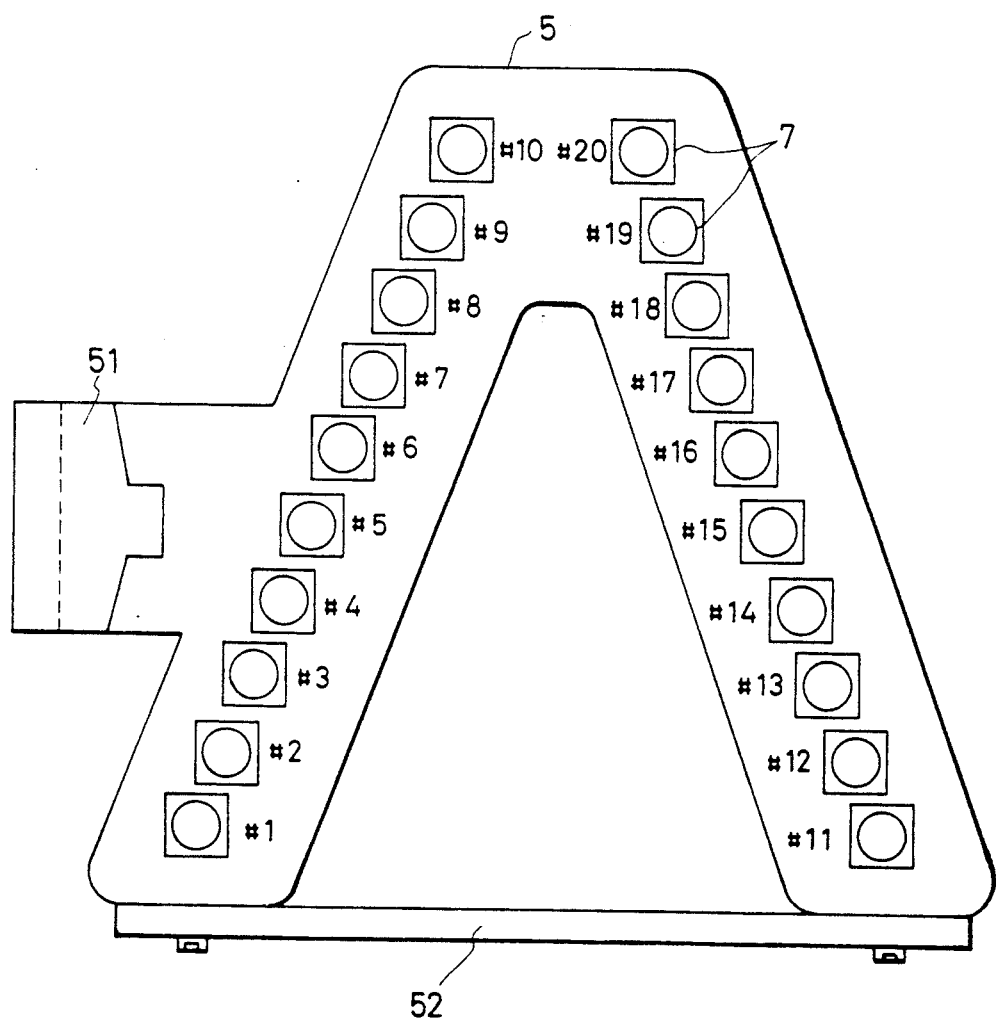
FIGS. 4 and 5 are a plan view and an elevational view, respectively, of a probe support table and a probe support mechanism arranged on the table.
Figure 5:
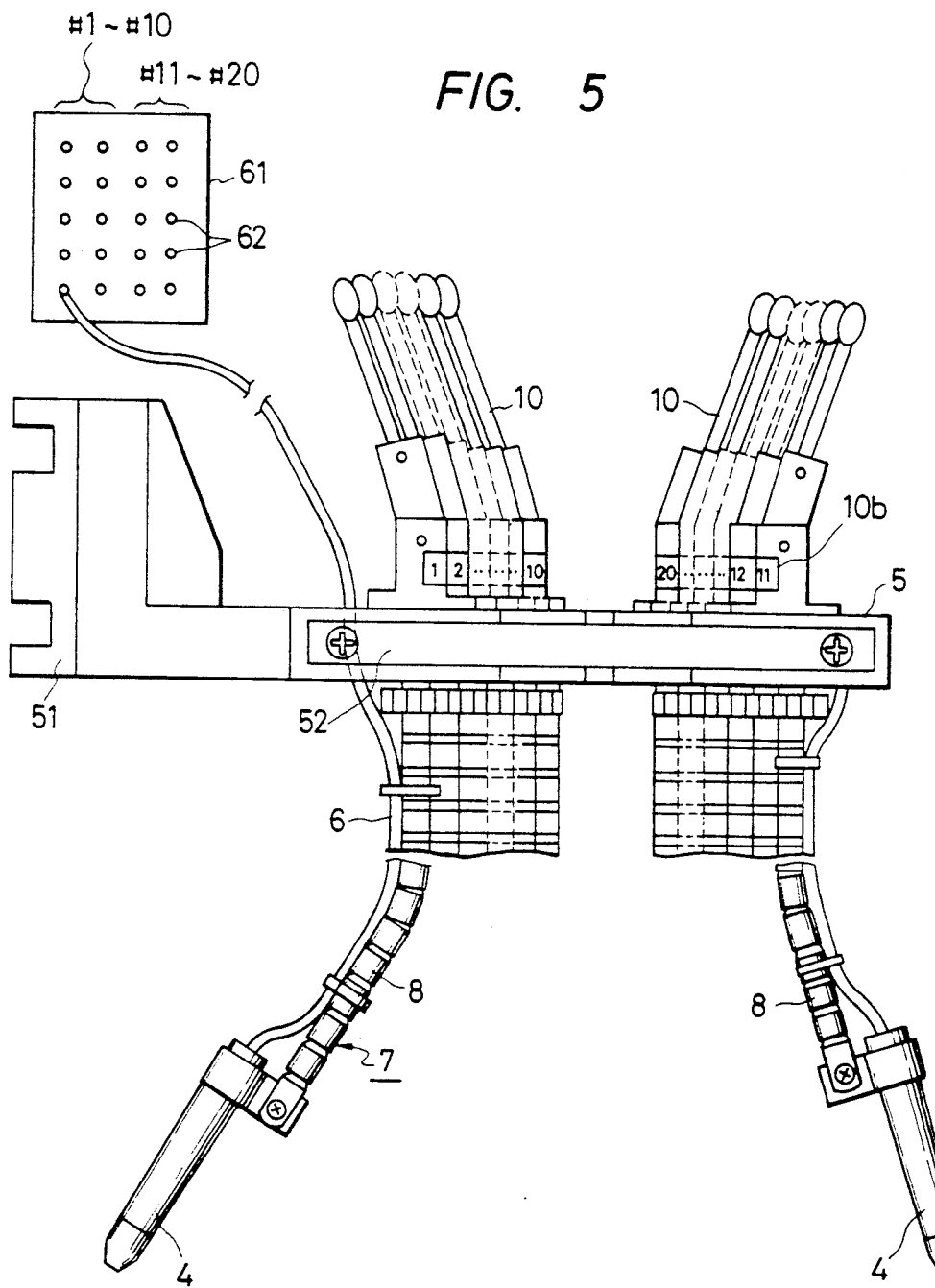

FIGS. 4 and 5 are schematic diagrams of the probe support table and the multichannel probes arranged together. FIG. 4 is a plan view of a V-shaped probe support table 5. The handgrip 52 is attached to the front edge opposite to the apex of the V-shaped table. If the probes of 20 channels are disposed as illustrated in FIG. 4, discrete channel numbers #1–#20 are given to the probes. These channel numbers correspond to the selective switches of the control board 3. The multichannel probes 4 are divided into two groups: #1–#10 and #11–#20 in numerical order of the channel. The first group #1–#10 and the second group #11–#20 are arranged on the left-hand side and right-hand side, respectively, of the V-shaped probe support table 5 together with the respective support mechanisms. As viewed by the operator, the multichannel probe support mechanisms are arranged in the numerical order of the channels and in the form of a "V" on the probe support table 5. In this case, a display label 10b marked with the channel number is attached to the base of the corresponding clamp lever 10 located on the surface of the probe support table 5.

Since the two groups of probes are disposed on the left-hand and right-hand sides as viewed from the operator, the multichannel numbers 10b may be easily checked visually from one side. In addition, the position of the clamp levers 10 of the probe support mechanism 5 provide a visual indication as to whether the support mechanism 8 of the corresponding multichannel probe 4 has been locked or released.

The connecting terminals 62 of the multichannel probe are disposed on the terminal plate of an intermediate cord connector box 61 in numerical order #1-#20 of the channels corresponding to the groups of probes. The cord 6 of the probe 4 corresponding to each of the channel numbers is connected to the corresponding connecting terminal 62. In that state, the operator may rotate each clamp lever 10 to the lock position to lock the flexible pipe 8 in the operative orientation. The probes of the selected channels may be easily and accurately applied to the area or areas of the body one after another to complete the probe settings.

The operator then sets for each probe 4 the optimum irradiation mode including a laser irradiation output, irradiation time, etc., which are dependent on which body part is being treated as well as the condition of the affected body part, and turns on the selective switch 32 and the irradiation start switch 37, so that the irradiation of laser beams from the probes 4 is started. Whether the laser beams are irradiated from the probes of the selected channels simultaneously and collectively or are successively switched on one after another in a given order can be selected according to programming on the control board 3. Moreover, the irradiation display lamps 33 are caused to blink during laser beam irradiation and, when the laser beam irradiation is terminated after a set period of time has elapsed, the lamps 33 are turned off. The doctor or operator may also request through the control board that the various therapeutic items be printed by the printer 38. The flexible pipes 8 supporting the probes 4 are restored to the free or unrestricted positions by rotating each clamp lever of the probe support mechanism to the release position.

As set forth above, the probes are divided into two groups in numerical order of the discrete channels specified on a probe basis and the probe support mechanisms are put into the left-hand and right-hand sides of the probe support table 5 in two, opposite rows. The selection of the probes when treatment is applied and the setting of the irradiation mode on the control board 3 in coordination of the selected probes can be readily checked visually to prevent operation errors. Moreover, by adjusting the groups of probes 4 distributed to the left and right to different body parts, for example the left and right hands of the patient, the probes can be easily and effectively used to treat several affected body parts.

Figure 6:
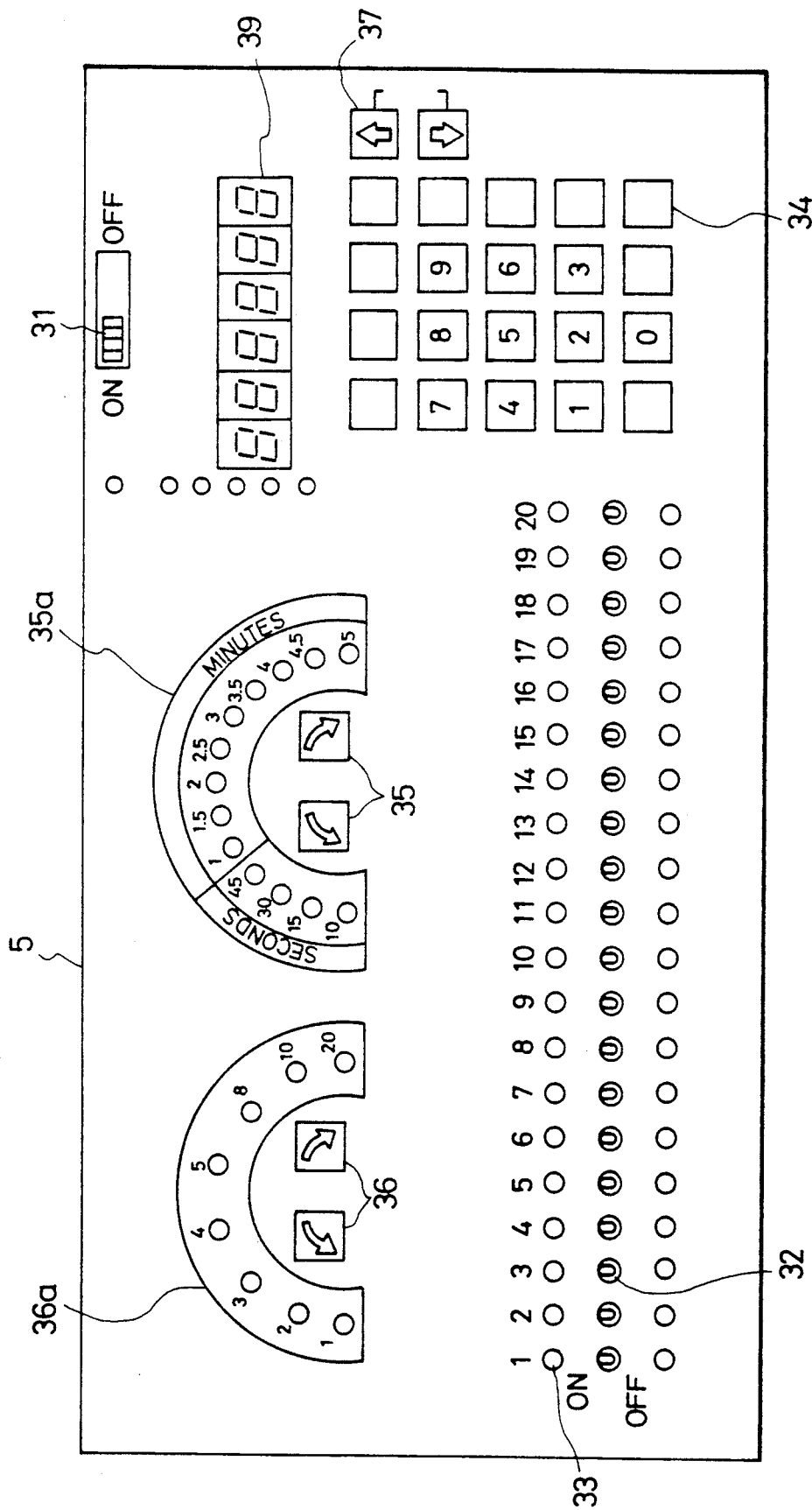
FIG. 6 is a layout drawing of an operating plate of a control board.

As shown in FIG. 1, the control board 3 is equipped with the power supply, various control devices, and the operating panel for setting the irradiation mode. As shown in FIG. 6, the operating panel includes, on its front panel, the power supply switch 31 the irradiation selective switches 32 corresponding to the multichannel probes (e.g., #1-#20), the irradiation display lamps 33, various function keys 34 including numerical keys, the keys 35 for setting the laser beam irradiation time and the relative scale plate 35a, the grouping keys 36 for dividing the multichannel (#1-#20) probes into more than one group and setting the relative scale plate 36a, the laser beam irradiation setting keys 37, and the display 39 for displaying various items of data. The alarm lamps indicate irregularities in the multichannels corresponding to the selective switches 32. Moreover, a printer (not shown in FIG. 6) may be provided for printing out various therapeutic data including patient numbers, doctor numbers, therapeutic dates, and conditions of the irradiation mode. The aforesaid function keys 34 include an irradiation start key, a termination key, a patient key, a doctor key, a clock key, a writing key, a printing key, a clear key, and a selective irradiation start key for selecting whether all the groups are to start simultaneously or in a group order when laser beam irradiation is to be accomplished by groups of probe 4.

The control board 3 and the multichannel probes 4 are mutually respectively connected through the wiring cords 6 and the multichannel probes 4 are collectively supported by the probe support table 5 through the probe support mechanisms 7. Each probe support mechanism 7 is an assembly of the flexible pipe 8 as a support arm having a front end for supporting the probe 4 on a channel basis and a back end attached to the undersurface of the probe support table 5.

Procedures for the operation of the laser therapeutic apparatus during the actual provision of treatment and for the operation of setting the laser beam irradiation mode will now be described. In the therapeutic standby state, the clamp lever 10 of the probe support mechanism is set in the release position and each of the multichannel probes 4 is suspended from the undersurface of the probe support table 5 in the unrestricted state through the support arm. The power supply is held off in the control board.

As described above, the patient reclines on the bed 1, and the doctor or operator manipulates the handgrip 52 of the probe support table 5 to move the probe support table 5 to a suitable position for treatment of a specific body part or parts or proximate an effective spot for treatment, e.g., the shoulder, the knee, the knee and ankle joint regions, etc. Subsequently, the operator selects the probes for use from those suspended from the probe support table 5 in the numerical order of the channels and bends the support arms 8 until the laser beam irradiation end of each probe 4 is close to, or in contact with, the affected body part or the effective spot for treatment e.g., the finger or toe joint. In that state, the operator rotates each corresponding clamp lever to the lock position and locks the support arms in the bent posture. The probes of the selected channels are thus applied to the affected parts one after another to complete the probe setting.

The operator then programs the setting for the irradiation mode including the optimum laser irradiation output, the irradiation time, etc. As stated above, these factors depend on what the affected body part is and on the condition of the affected body part. More specifically, the operator may first press the function keys 34 to enter a patient number, a charged doctor number, and a therapy date. Relative to the multichannels #1-#20, the operator may set a grouping number by properly operating the grouping keys 36. If the selected grouping number is 5, for instance, the multichannel probes 4 are divided into four groups of five probes each, i.e., #1-#5, #6-#10, #11-#15, and #16-#20 and, according to the setting operation, each group is simultaneously set to the same irradiation mode on a group basis. Subsequently, the laser beam irradiation time and the laser beam irradiation output are respectively set by means of time setting keys 35 for each group and the selective switches 32 corresponding to the selected multichannel probes to be turned on. Moreover, whether all of the groups of laser beam irradiation probes are simultaneously started or whether the groups are individually and successively energized in a desired group order is selected by means of the simultaneous or sequential key among the function keys and, when the start key is pressed, the laser beams are irradiated to the affected body parts through the probes 4 in accordance with the specified irradiation mode. The irradiation display lamps 33 correspond to the probes selected and are appropriately turned on during the laser beam irradiation.

When the laser beam irradiation is interrupted because of a malfunction in a probe during irradiation, the alarm lamp corresponding to the malfunctioning probe blinks to indicate the irregularity. When the laser beam irradiation is terminated after the set time has lapsed, the lamp is turned off and simultaneously various therapeutic items are printed out on blank forms by the printer 38. If the termination key is pressed during operation, all laser irradiation is stopped. By rotating the clamp levers 10 for the probe support mechanisms 7 to the release position after the laser beam irradiation is terminated, the relevant probes will be reset to the therapeutic standby position.

In the multichannel style laser therapeutic apparatus described above, a plurality of probes are attached to the control board, the control board is provided with probe selective means for causing irradiation through the selected probes, group setting means for dividing the selected probes into more than one group, and an exposure setting means for setting the laser irradiation time and the irradiation output for each group defined by the group setting means. Accordingly, the proper laser beam irradiation mode can be set for each of the multichannel probes in a short time and both simply and efficiently. In consequence, the operation of the therapeutic apparatus is simplified and therapeutic efficiency is increased.

FIGS. 7, 8, 9, 10 are block diagrams of different probes for use with the present invention.

Figure 7:
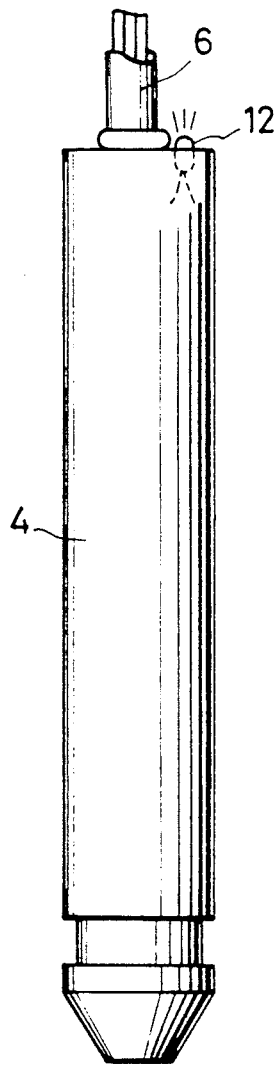
FIGS. 7, 8, 9, and 10 are external side and top views of different embodiments of laser probes according to the present invention.
Figure 9:
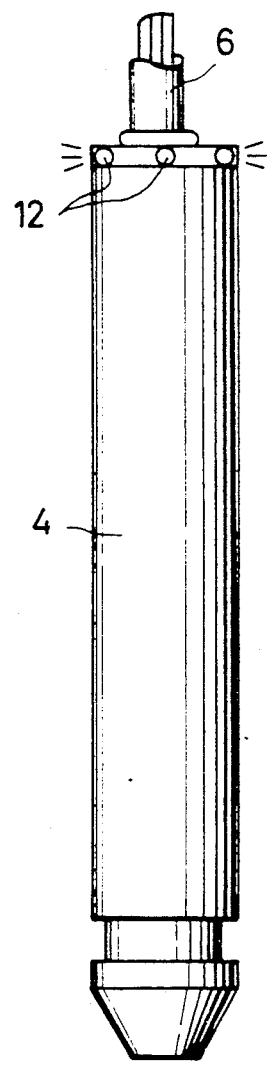
Figure 8:
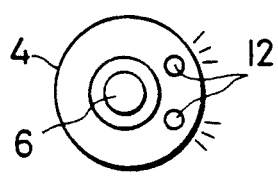
Figure 10:
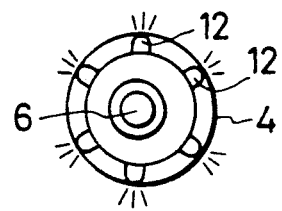

According to the embodiment of FIGS. 7 and 8, a plurality (two in the case of this example) of light emitting diodes 12 are mounted in the upper end face of the body of a probe 4 to display the state of the laser beam irradiation. Each light emitting diode 12 is connected to the drive circuit (not shown in FIGS. 7 and 8) of a laser diode within the probe 4. The drive circuit turns the corresponding diodes 12 on when the laser beam is to be irradiated, and turns the diodes 12 off when no laser beam irradiation is desired or when laser beam irradiation is stopped because of trouble with a laser diode during laser beam irradiation. In the case of the embodiment shown in FIGS. 9 and 10, a plurality of parallel diodes 12 are installed as display lamps in the peripheral face of the probe body, for example, in the form of a ring.

Each of the multichannel probes 4 is equipped with the diode display lamp, which is contained in the probe body, for displaying the state of laser beam irradiation. It therefore becomes unnecessary to check by means of the control boards whether a probe has been actuated to determine that the corresponding laser beam is being irradiated. Instead, the operation of each probe can be confirmed readily by visually inspecting the display lamp or lamps fitted near the end of the probe. Consequently, not only the operability but also the controllability of the laser therapeutic apparatus is improved.

FIG. 11 is a detailed sectional block diagram of the probe and FIG. 12 is an illustration of the probe during operation.

The probe 4 is, as shown in FIG. 11, an assembly of an outer cylinder 41, an inner movable cylinder 42 fitted into and supported within the outer cylinder 41, a laser head 43 installed in the inner cylinder 42, an end cap 44 fixed to the top of the outer cylinder 41 and a compression spring 45 held between the end cap 44 and the upper end of the inner cylinder 42. The laser diode 43 comprises a diode 46, a printed circuit board 47 that includes various conventional semiconductor chips used as the driver circuit of the diode 46, one or more optical lenses 48, and a lens-barrel 49 containing the diode 46 and lenses 48 and interlockingly inserted in the inner cylinder 42. In addition, a spacer 49a is provided between the lenses 48, and the printed circuit board 47 is mounted on an extension of the upper edge of the lensbarrel 49.

The inner cylinder 42 has a laser irradiation port 42a at its front end and an elongated groove 42b in its peripheral side face, for use as a guide in the vertical direction. A screw 42c connects a side wall surface of the end cap 44 and the outer cylinder 41 and is fitted into the groove 42b to act as a guide. The wiring cord 6 passes through the end cap 44 into the probe 4 where it is connected to the printed circuit board 47. In the probe 4 thus constructed, the inner cylinder 42 containing the laser head 46 is supported for movement in the vertical direction relative to the outer cylinder 41 and is urged downwardly by the spring 45.

As set forth above, each of the multichannel probes collectively supported by the probe support table 5 through the support mechanism is equipped with the outer cylinder 41 supported in such a manner as to fit the probe to the support mechanism. The inner cylinder 42 is fitted into the outer cylinder 41 for relative movement in the axial direction. The laser head is mounted at the front end of the inner cylinder 42. The spring member is held between the outer cylinder 41 and the rear end of the inner cylinder 42 and is used to bias the inner cylinder 42 together with the laser head at all times to prevent the probe 4 from drifting off or shifting from the affected body part even if the body part is slightly moved. This is because each probe is arranged to follow the motion of the patient's body and to cause the laser beam irradiation end to remain in contact with the corresponding affected body part or effective spot for treatment. This further increases operating reliability.

Figure 13:
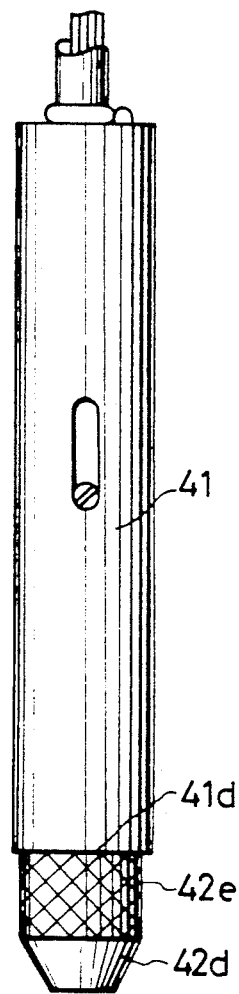
FIGS. 13, 14 and 15 are external views of the principal parts of different embodiments of probes according to the present invention, wherein the front end of the inner cylinder of the probe includes a colored portion (FIG. 13), colored rings (FIG. 14), and grooves (FIG. 15)
Figure 14:
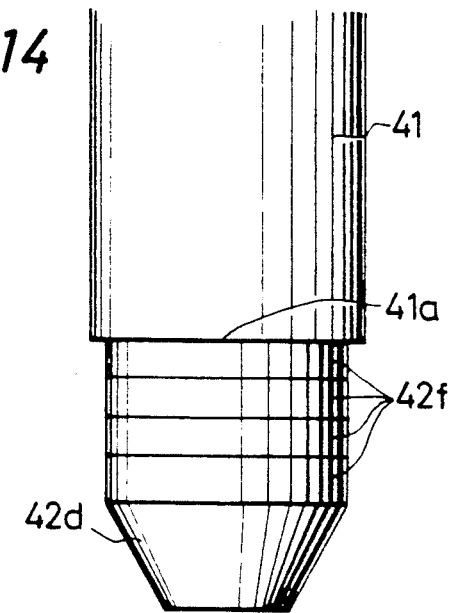
Figure 15:
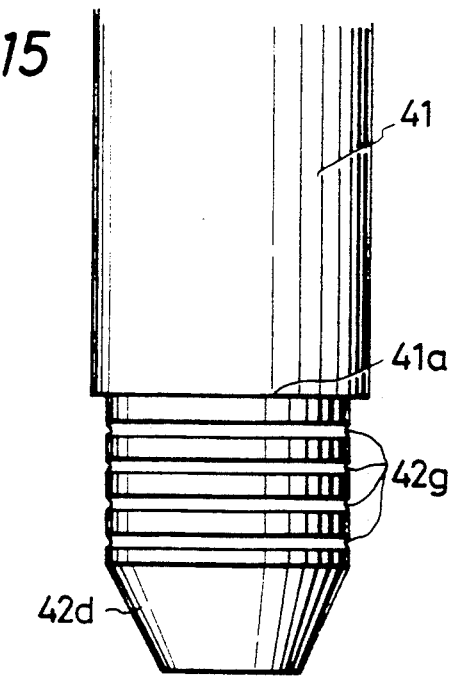

The front end 42d of the inner-cylinder may include a colored portion 42e as shown in FIG. 13 or bear an assortment of different colors in the form of color rings 42f as shown in FIG. 14. The end of the probe may also be provided with grooves 42g in the form of rings as shown in FIG. 15 to ensure that the proper setting of the probe against the affected body part can be visually confirmed with ease. The relative pressure exerted by the probe 4 on the body part as treatment spot can be determined by the amount of colored portion 42e or the number of rings 42f or grooves 42g visible when the probe is in the treatment position.

Figures 16, 17, 18:
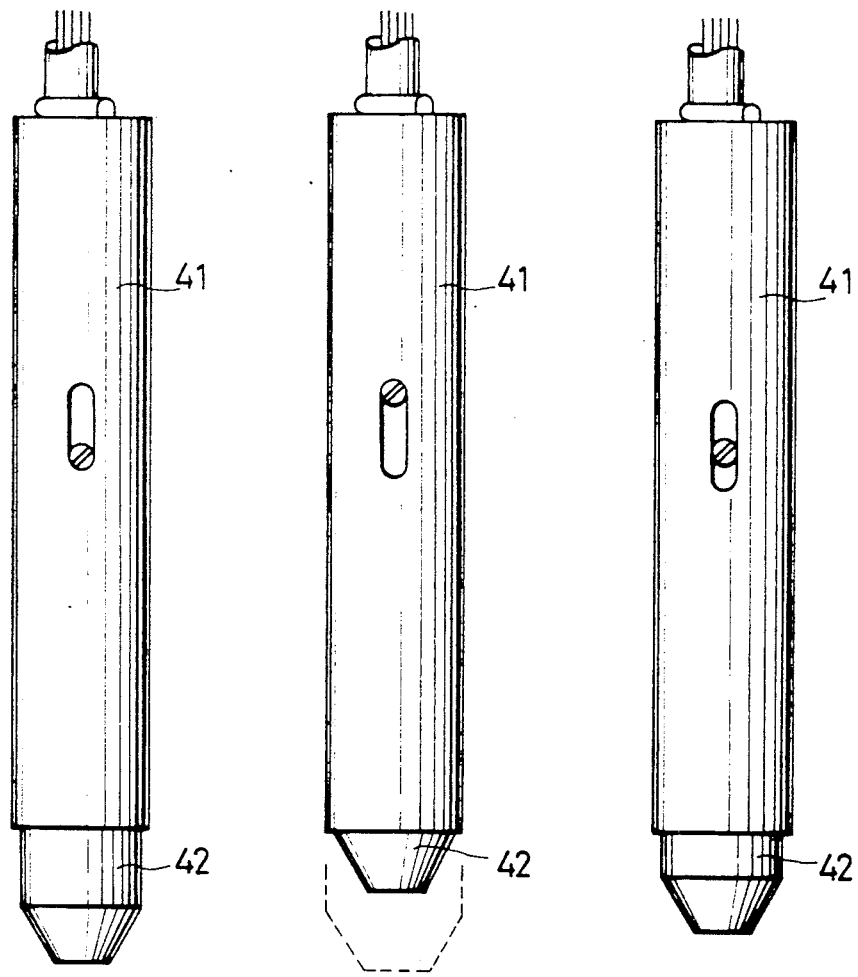
FIGS. 16, 17 and 18 are external views of different conventional probes in various degrees of extension.

Probes of the prior art are shown in FIGS. 16-18 and are such that the state in which the probe is normally set is equivalent to the state where the spring member applying pressure to the inner cylinder 42 is extended. Other probes are normally in a state where the spring member has not yet been extended. as shown in FIG. 17. or where the spring member is partially extended. as shown in FIG. 18. Those two cases are hardly distinguishable from one another externally and it is practically impossible to measure the extended quantity of the spring member if a large number of probes is provided.

According to the present invention. each of the multichannel probes is collectively supported by the probe support table 5 through the support mechanism 7 and is equipped with the outer cylinder 41 supported in such a manner as to fit the probe to the support mechanism. The inner cylinder 42 is guided in the axial direction by the outer cylinder 42. The laser head is mounted at the front end of the inner cylinder 42, the spring member is held between the outer cylinder 41 and the rear end of the inner cylinder 42 and is used to bias the inner cylinder together and the laser head away from the cap 44 at all times, and an identifier is provided for identifying the movement of the inner cylinder 42 in opposition to the spring member and in the axial direction in relation to the outer cylinder. Each of the multichannel probes can be properly set for treatment of a given affected body part or effective treatment spot of the patient and the properly set state can also be confirmed quite easily in a visual manner. The probe is prevented from drifting off or shifting from the affected body part even if the patient's body is moved slightly after the multichannel probes have been set to the prescribed affected body parts or the spots of the patient for effective treatment. Each probe 4 is arranged to follow the motion of a patient's body and to cause its laser beam irradiation end 42a to remain in contact with the affected body part or effective spot for treatment.

Referring now to FIGS. 19 through 24. a control method will be described for treatment by irradiating laser beams to affected body parts of a patient by means of the laser therapeutic apparatus according to the present invention.

Figure 19:
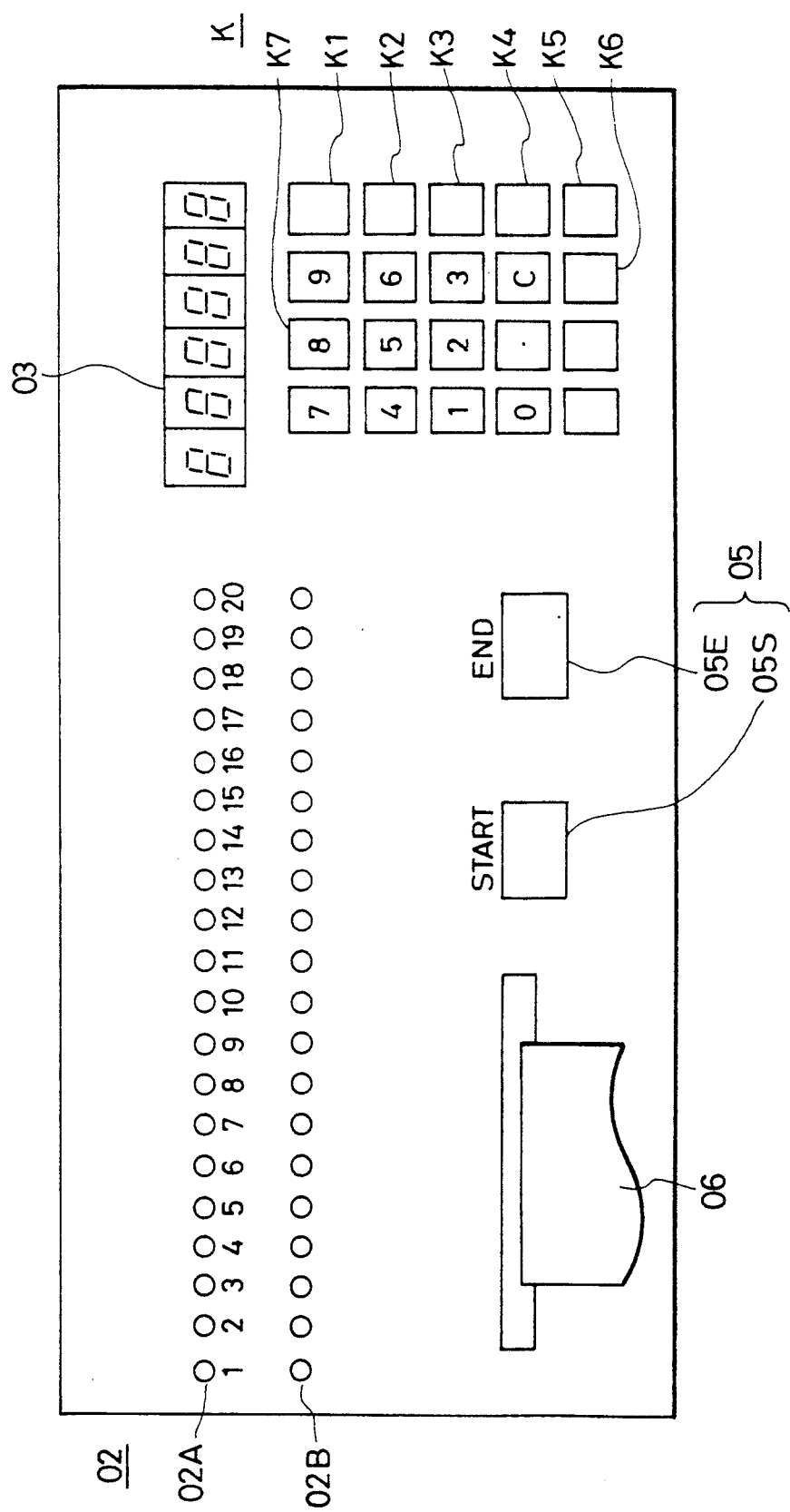
FIG. 19 is a layout drawing of an operating panel of a control board for a laser therapeutic apparatus embodying the present invention.
Figure 20:
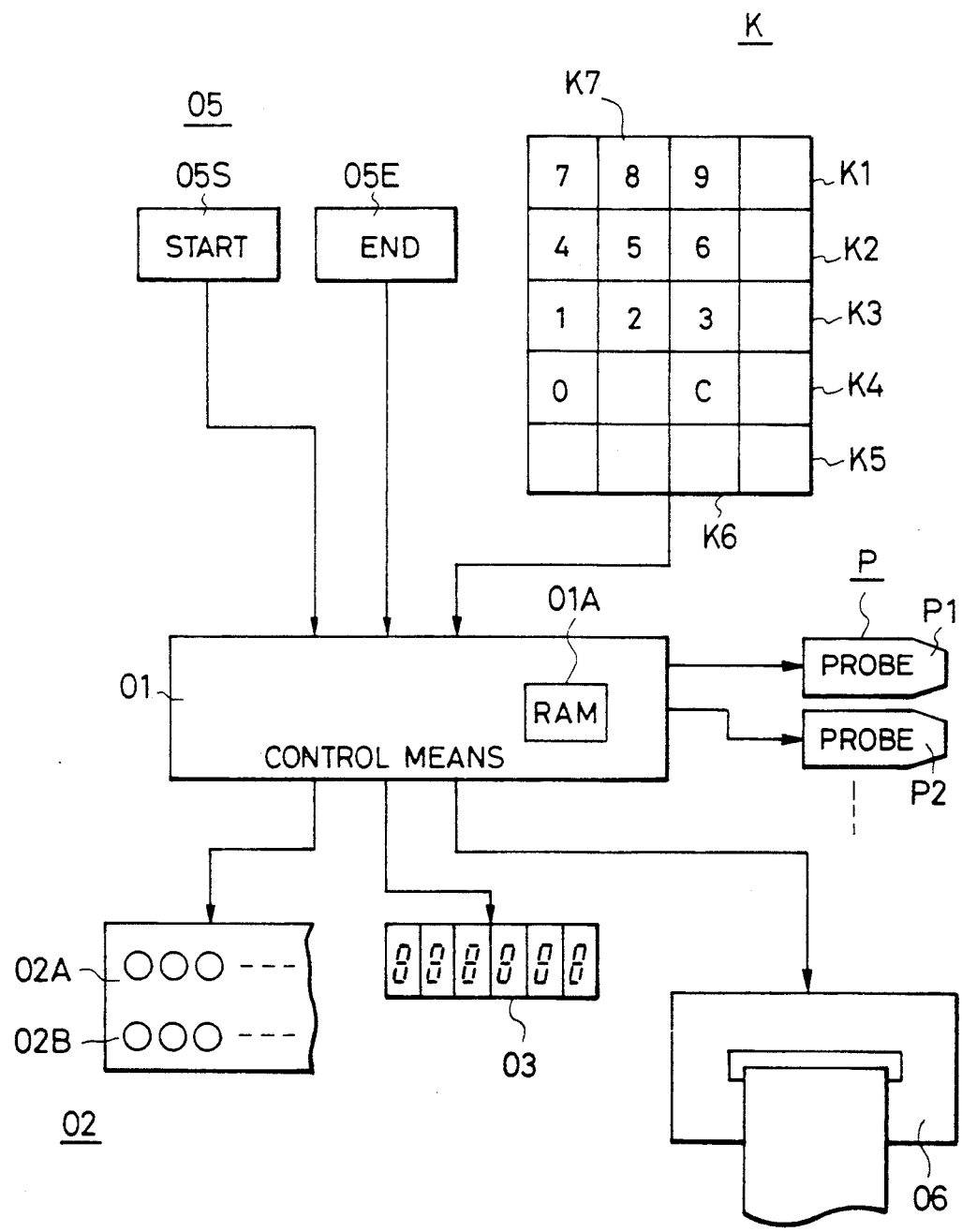
FIG. 20 is a schematic circuit block diagram of the control board of FIG. 19.
Figure 22:
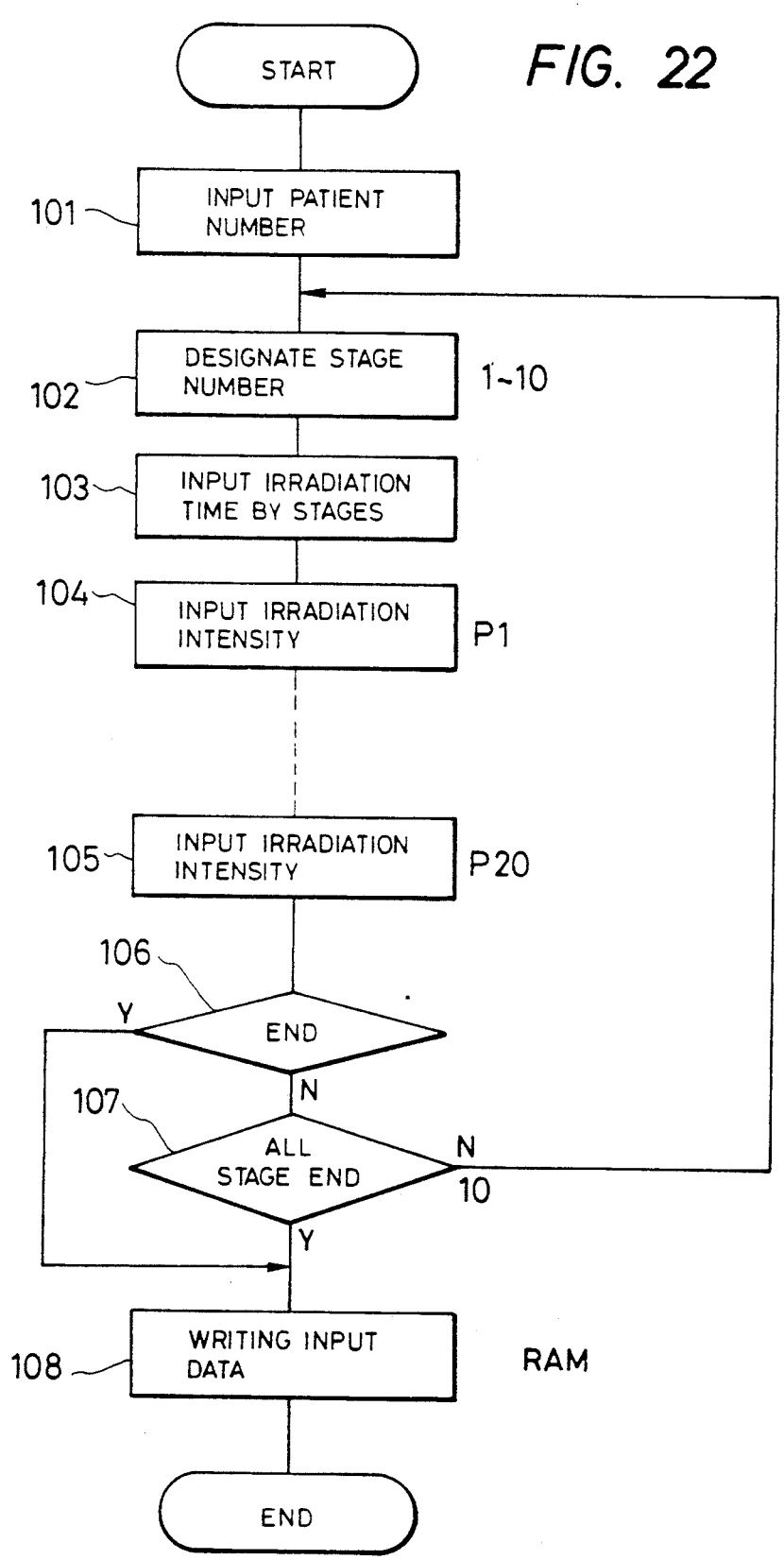
FIGS. 22, 23 and 24 are flowcharts showing procedures for the operation of the control board of FIG. 19.
Figure 23:
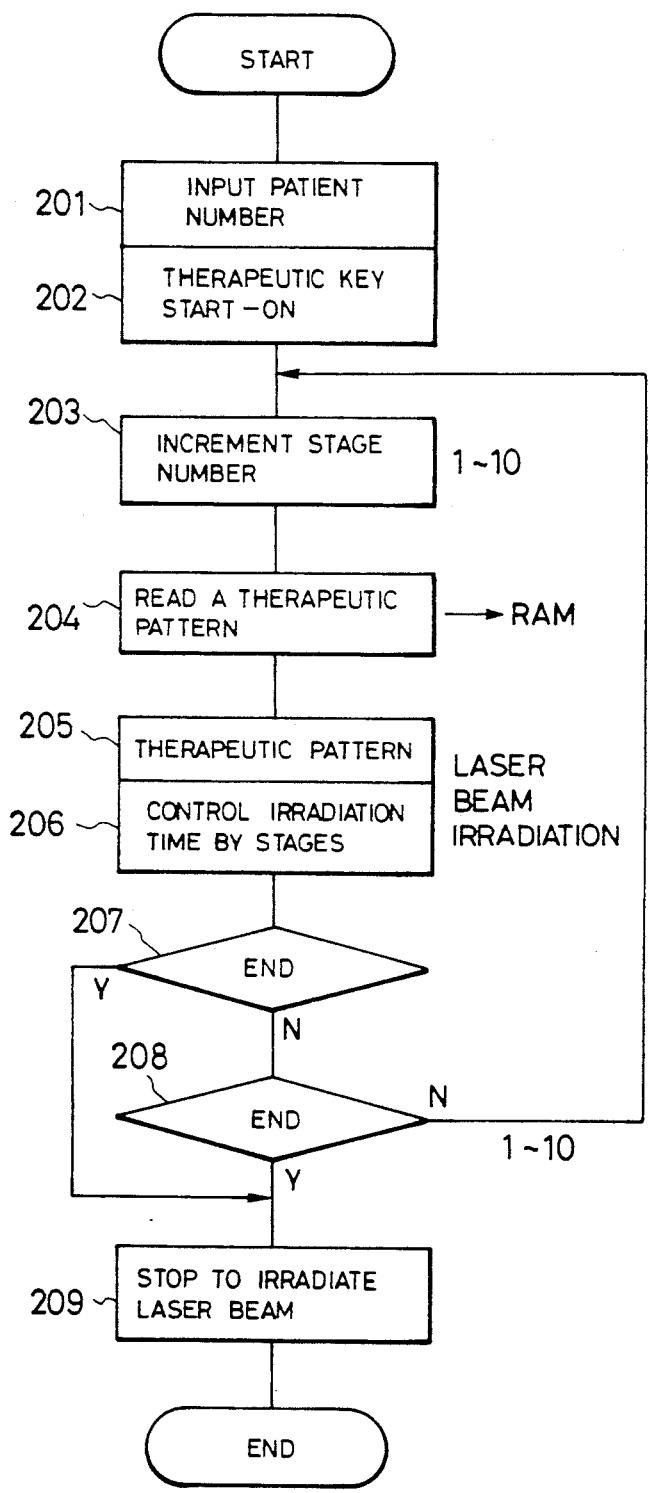
Figure 24:
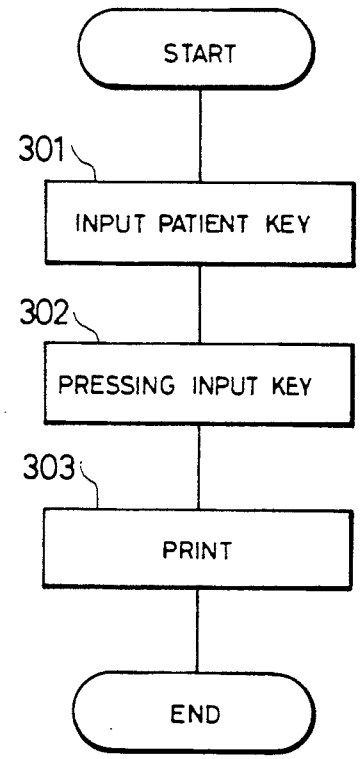

FIG. 19 is a layout drawing of an operating panel of a control board according to the present invention. FIG. 20 is a schematic block circuit diagram of the control board. FIG. 21 is an illustration of a selected therapeutic pattern. FIGS. 22 through 24 are flow charts showing procedures for the operation of the control board of FIG. 20. More specifically. FIG. 22 is a procedure for setting a therapeutic pattern setting mode, FIG. 23 is a procedure for setting a therapeutic operating mode, and FIG. 24 is a procedure for setting printing mode of the printer.

The control panel 3 is shown in FIG. 19 and includes a power supply, a variety of control devices, and an operating panel for setting the therapeutic pattern for laser beam irradiation.

The operator instructs the patient to recline on the bed and adjusts the location of the probes P to be properly positioned with respect to the affected body parts that are to be treated. The patient is treated in accordance with the therapeutic pattern (described later) being newly set or already set for the patient. Further a supplementary explanation will be given of the procedure for applying the probes P to the patient.

In the therapeutic standby state, the clamp lever of each of the probe support mechanisms 7 is set in the release position and each of the multichannel probes 4 is movably suspended from the undersurface of the probe support table 5. Subsequently, the operator selects the probes P for use from those suspended from the probe support table 5 in numerical order of the probes (channels) and bends the corresponding support arms to position the laser beam irradiation end of each probe 4 close to, or in contact with, the affected body part or the effective spot for treatment, e.g., a finger or a toe joint. In that state, the operator rotates each clamp lever 10 to the lock position to lock the positions of the support arms. The probes P of the selected channels are thus set to the affected parts one after another to complete the probe setting.

Referring to FIG. 19, irradiation lamps 02A comprise a state display lamp 02 and are used to display the states of the probes P (P1-P20). Alarm lamps 02B are lit to indicate trouble on an individual probe basis.

A numerical display 03 is used to display various set values and an operating keyboard K consists, as described in detail by reference to FIG. 20, of function keys K1-K6 for setting patient numbers, stage numbers, irradiation time by stages, irradiation intensity by stages and probes, etc., and a numerical keyboard K7.

A therapeutic switch 05 consists of a therapeutic start switch 05S and a therapeutic termination switch 05E for respectively giving instructions as to the commencement and termination of treatment. A printer 06 is used to print out the contents of the set data as well as other data.

FIG. 20 is a block circuit diagram of the control board, wherein there is shown control means 01 consisting of a CPU and including a ROM (not shown) and a RAM 01A.

The CPU receives signals from the operating keys K1-K7 and the therapeutic switch 05. and produces signals for driving the probes P, the state display lamps 02. the numerical display 03, and the printer 06.

Under actual treatment. the laser beam irradiation intensity and the irradiation time are selected to vary among the probes P1-P20, which may also be set to differ in irradiation order, so that a therapeutic pattern can be established for each patient. The therapeutic pattern corresponding to the patient number is stored in the RAM 01A and, therefore, a therapeutic pattern can be recalled and reapplied by merely designating the patient number when the same patient is being treated.

A therapeutic pattern, as shown in FIG. 21, is employed to set the length of the irradiation time TS on the basis of individual stage numbers NS, and the irradiation intensity for each of the probes P1-P20 by dividing the therapeutic time for one patient at one time into 10-stage lengths of the irradiation time TS corresponding to the numerical values 1-10 of the stage numbers NS. The irradiation intensity may be set at any one of ten levels. The therapeutic pattern may be printed out by the printer 06, and are stored in the RAM 01A that is composed of semiconductor memory elements backed up by a battery.

Referring to a flowchart of FIG. 22 in addition to FIGS. 19, 20, and 21, a procedure for the operation of setting the therapeutic pattern of FIG. 21 will be described. A patient number is entered using the patient number key K1 and the numerical key board K7 (STEP 101). The patient number may be selected to represent symptoms. Subsequently, a designated stage number NS is supplied using the stage number key K2 and the numerical key board K7 (STEP 102). Then, irradiation time TS by stage number is supplied using the time keyboard K3 and the numerical keyboard K7 (STEP 103).

Laser beam irradiation intensity set for the probes P1 through P20 is supplied using the probe number key K4 and the numerical keyboard K7 (STEP 103-105) and the therapeutic pattern for one stage number NS is thus completed. When writing key K6 is pressed after the input operation of STEPs 102-105 up to the stage numbers 1-10 is completed, the control means 01 writes the input data of the total therapeutic pattern by stages to the RAM 01A as regular set data.

Referring to the flowcharts of FIGS. 23 and 24 in addition to FIGS. 19, 20, and 21, procedures for the operation of setting therapeutic and printing modes will be described.

In FIG. 23, when the therapeutic start key 05S is turned on (STEP 202) after a patient number is supplied using the patient number K1 and the numerical keyboard K7 (STEP 201), the control means 01 increments the stage number and reads the therapeutic pattern (FIG. 21) at the stage number NS value 1 relative to the patient number involved from the RAM 01A (STEPs 203, 204). Then the control means 01 causes the probes P1-P20 to output the irradiation intensity set to each of the probes P1-P20 in the pertinent therapeutic pattern during the irradiation time TS by stages corresponding to the relevant stage number NS (STEPs 205, 206).

The operations at STEPs 203-206 up to the stage numbers 1-10 are repeated and, when the laser beam irradiation in the therapeutic patterns relative to all of the stage numbers is terminated, the control means 01 causes the laser output to stop (STEPs 208, 209).

When the printing operation shown in FIG. 24 is started, the printing key K5 is pressed after the patient number is supplied using the patient number key K1 and the numerical keyboard K7 as in the case of STEP 101 of FIG. 23. Then the control means 01 drives the printer 06, which prints out the therapeutic pattern data corresponding to what is shown in FIG. 21 by patient and stage numbers set and stored in the RAM 01A (STEPs 301, 302, 303).

The multichannel type laser therapeutic apparatus with a plurality of probes attached to the control board according to the resent invention utilizes the patient number key K1 for setting patient numbers as data for selectively designating specific patients or symptoms, the stage number key K2 for setting the stage numbers, NS, as data for selectively designating each of the predetermined irradiation stages provided on a patient number basis, the time key K3 for setting laser irradiation time TS, common to each of the probes on a stage number basis, the probe number key K4 for setting laser beam irradiation intensity for each probe within the irradiation time by stages, the therapeutic start switch 05S for giving laser beam irradiation start instructions, and the control means 01 for causing laser irradiation by stages corresponding to one of the stage numbers belonging to the symptom number involved.

What is claimed is:

1. A laser therapeutic apparatus comprising:
a power supply for supplying power;
a plurality of laser probes operatively coupled to said power supply and selectively activated to convert the power to beam radiation;
control means operatively coupled to said laser probes for selecting an irradiation time and an irradiation output for each of said laser probes and for controlling activation of said laser probes in accordance with the selected irradiation times and irradiation outputs;
a probe support table having a rigid substantially planar surface to which each of said laser probes is movably coupled so that said laser probes are movable in two dimensions, said probe support table selectively positioning and supporting said plurality of laser probes in spaced relation; and
positioning means coupled to said probe support table for selectively positioning said probe support table.

2. A laser therapeutic apparatus according to claim 1, wherein said positioning means comprises:
a first support member having first rails extending in a first direction to which said probe support table is movably coupled to move in said first direction; and
a second support member having second rails extending in a second direction substantially perpendicular to said first direction to which said first support member is movably coupled to move in the second direction.

3. A laser therapeutic apparatus according to claim 1, wherein each of said laser probes includes a laser head, an outer cylinder, an inner cylinder fitted into said outer cylinder to be slidably movable in a longitudinal direction with respect to said outer cylinder, a laser head support member for supporting said laser head, and a tensioning member disposed between said outer cylinder and said inner cylinder for applying tension to force said inner cylinder in the longitudinal direction with respect to said outer cylinder.

4. A laser therapeutic apparatus according to claim 3, wherein each of said laser heads comprises:
a lens barrel;
a laser diode mounted to said lens barrel for generating one of the laser beams and directing the laser beam along an optical path;
a laser diode driving circuit mounted to said lens barrel and coupled to said laser diode for driving said laser diode; and
at least one lens mounted to said lens barrel and disposed in the optical path of the laser beam;

5. A laser therapeutic apparatus according to claim 3, wherein
each of said laser probes comprises an identifying portion on said inner cylinder for indicating a magnitude of longitudinal movement of said inner cylinder with respect to said outer cylinder.

6. A laser therapeutic apparatus according to claim 5, wherein said laser head comprises:
a lens barrel;
a laser diode mounted to said lens barrel for generating one of the laser beams and directing the laser beam along an optical path;
a laser diode driving circuit mounted to said lens barrel and coupled to said laser diode for driving said laser diode; and
at least one lens mounted to said lens barrel and disposed in the optical path of the laser beam.

7. A laser therapeutic apparatus according to claim 5, wherein said identifying portion comprises a plurality of colored portions provided on a portion of said inner cylinder which protrudes from an end of said outer cylinder.

8. A laser therapeutic apparatus according to claim 5, wherein said identifying portion comprises a plurality of grooves on a portion of said inner cylinder which protrudes from an end of said outer cylinder.

9. A laser therapeutic apparatus for treating a patient by irradiating selected body parts of the patient with laser beams, said apparatus comprising:

a plurality of laser probes, each of said laser probes including a laser head for generating one of the laser beams;

control means operatively coupled to each of said laser heads for individually energizing and controlling each of said laser heads;

a probe support table having a rigid substantially planar surface to which each of said laser probes is movably coupled so that said laser probes are movable in two dimensions, said probe support table selectively positioning and supporting said laser probes in spaced relation, a first portion of said laser probes being coupled to said probe support table in a first group and a second portion of said laser probes being coupled to said probe support table in a second group, said control means energizing and controlling said laser probes in said first group separately from said laser probes in said second group; and positioning means coupled to said probe support table for selectively positioning said probe support table.

10. A laser therapeutic apparatus according to claim 9, wherein said probe support table comprises a V-shaped member having a left-hand portion and a right-hand portion, said first group of laser probes being distributed on said left-hand portion and said second group of laser probes being distributed on said right-hand portion.

11. A laser therapeutic apparatus according to claim 10, further comprising:
a plurality of flexible support arms movable in the two dimensions for individually coupling said laser probes to said probe support table, each of said flexible support arms being associated with a corresponding and respective one of said laser probes and having a first end coupled to said laser head of the associated laser probe and a second end coupled to said V-shaped member; and a plurality of clamping mechanisms, each of said clamping mechanisms being associated with a corresponding and respective one of said flexible support arms for selectively locking said associated support arm in a selected orientation and selectively unlocking said associated support arm to enable the free movement thereof.

12. A laser therapeutic apparatus for treating a patient by irradiating selected body parts of the patient with laser beams, said apparatus comprising:
a plurality of laser probes, each of said laser probes including a laser head for generating one of the laser beams;

control means operatively coupled to each of said laser heads for individually energizing and controlling each of said laser heads;

a probe support table having a rigid substantially planar surface to which each of said laser probes is movably coupled so that said laser probes are movable in two dimensions, said probe support table selectively positioning and supporting said laser probes in spaced relation;

positioning means coupled to said probe support table for selectively positioning said probe support table;

a plurality of flexible support arms movable in the two dimensions for individually coupling said laser probes to said probe support table, each of said flexible support arms being associated with a corresponding and respective one of said laser probes and having a first end coupled to said laser head of the associated laser probe and a second end coupled to said probe support table; and a plurality of clamping mechanisms, each of said clamping mechanisms being associated with a corresponding and respective one of said flexible support arms, for selectively locking said associated support arm in a selected orientation and selectively unlocking said associated support arm to enable free movement of said support arm.

13. A laser therapeutic apparatus according to claim 12, wherein:
each of said flexible support arms comprises a flexible pipe including a plurality of serially-connected pipe segments forming an elongated flexible joint; and each of said clamping mechanisms includes an elongated connector and tensioning means for selectively applying tensions to said connector, said connector having a first end connected to one end of said associated flexible pipe and a second end connected to said tensioning means, each of said clamping mechanisms being positioned in a first position for locking said associated support arm and positioned in a second position for unlocking said associated support arm.

14. A laser therapeutic apparatus according to claim 13, wherein each of said flexible pipes includes a base fitting member fixed to said probe support table and an adjusting screw cooperating with said base fitting member for variably adjusting the relative position of said flexible pipe with respect to said tensioning means of said associated clamping mechanism.

15. A laser therapeutic apparatus for treating a patient by irradiating selected body parts of the patient with laser beams, said apparatus comprising:
a plurality of laser probes, each of said probes including a laser head for generating one of the laser beams;

a probe support table having a rigid substantially planar surface to which each of said laser probes is movably coupled so that said laser probes are movable in two dimensions, said probe support table selectively positioning and supporting said laser probes in spaced relation;

positioning means coupled to said probe support table for selectively positioning said probe support table;

control means operatively coupled to each of said laser heads for selectively energizing and controlling said laser heads; and a plurality of display lamp means, each of said display lamp means mounted in and associated with a corresponding and respective one of said laser probes for indicating the state of energization of the laser head of said associated laser probe.

16. A laser therapeutic apparatus according to claim 15, wherein each of said display lamp means comprises a light emitting diode mounted near an end of said associated laser probe.

17. A laser therapeutic apparatus according to claim 15, wherein said display lamp means comprises a plurality of light emitting diodes formed in a ring at an end of said associated laser probe.

18. A laser therapeutic apparatus according to claim 15, wherein each of said display lamp means comprises a plurality of light emitting diodes mounted near the end of said associated laser probe.

19. A laser therapeutic apparatus for treating a patient by irradiating selected body parts of the patient with laser beams, said apparatus comprising:
- a plurality of laser probes, each of said laser probes including a laser head for generating one of the laser beams;
- a probe support table having a rigid substantially planar surface to which each of said laser probes is movably coupled so that said laser probes are movable in two dimensions, said probe support table selectively positioning and supporting said laser probes in spaced relation;
- positioning means coupled to said probe support table for selectively positioning said probe support table; and
- control means operatively coupled to each of said laser heads for individually energizing and controlling each of said laser heads, said control means including,
- probe selection means for selecting predetermined ones of said laser heads to be energized,
- probe group setting means for subdividing said selected laser heads into a plurality of groups wherein each laser head in a group is energized at the same time, and
- exposure setting means for selectively setting the laser irradiation time for each of said selected laser heads.

20. A laser therapeutic apparatus according to claim 19, wherein said control means includes irradiation start means for controlling said groups of laser heads and energizing said groups in one of a serial and a simultaneous mode.

21. A laser therapeutic apparatus for treating a patient by irradiating selected body parts of the patient with laser beams, said apparatus comprising:
- a plurality of laser probes, each of said laser probes having a laser head for generating one of the laser beams;
- a probe support table having a rigid substantially planar surface to which each of said laser probes is movably coupled so that said laser probes are movable in two dimensions, said probe support table selectively positioning and supporting said laser probes in spaced relation;
- positioning means coupled to said probe support table for selectively positioning said probe support table; and
- control means operatively coupled to each of said laser heads for individually energizing and controlling each of said laser heads, said control means including,
- symptom number setting means for setting symptom number data for selectively designating one of a plurality of patients and symptoms,
- stage number setting means for setting stage numbers as data for selectively designating each of a plurality of predetermined irradiation stages corresponding to at least one of the laser probes,
- irradiation time setting means for setting a laser irradiation time for each of the probes of each of said stages,
- irradiation intensity setting means for setting a laser beam irradiation intensity for each of the probes of each of said stages,
- irradiation start instructing means for entering start data for initiating irradiation by the laser probes, and
- laser beam irradiation executing means for energizing the laser probes of said laser stages in accordance with the symptom number data and in response to said start data and said irradiation intensity set by said intensity setting means stage number.

* * * * *